(12) United States Patent
Lewkowicz et al.

(10) Patent No.: US 7,907,986 B2
(45) Date of Patent: Mar. 15, 2011

(54) SYSTEM AND METHOD FOR CONTROLLING A DEVICE IN VIVO

(75) Inventors: Shlomo Lewkowicz, Kiryat Tivon (IL); Arkady Glukhovsky, Nesher (IL)

(73) Assignee: Given Imaging Ltd., Yoqneam (IL)

( * ) Notice: Subject to any disclaimer, the term of this patent is extended or adjusted under 35 U.S.C. 154(b) by 630 days.

(21) Appl. No.: 10/252,826

(22) Filed: Sep. 24, 2002

(65) Prior Publication Data
US 2003/0114742 A1 Jun. 19, 2003

Related U.S. Application Data

(60) Provisional application No. 60/324,067, filed on Sep. 24, 2001.

(51) Int. Cl.
*A61B 5/05* (2006.01)

(52) U.S. Cl. ............. 600/407; 348/68; 348/76; 348/77; 348/301; 348/370; 600/172; 600/476

(58) Field of Classification Search .................. 600/407, 600/424, 172, 476, 547, 153, 114, 350, 593, 600/582, 477, 109, 473, 160, 101; 348/68, 348/76, 77, 301, 370
See application file for complete search history.

(56) References Cited

U.S. PATENT DOCUMENTS

| | | | |
|---|---|---|---|
| 3,322,374 A | 5/1967 | King, Jr. | |
| 3,971,362 A | 7/1976 | Pope et al. | |
| 4,246,792 A | 1/1981 | Matzuk | |
| 4,278,077 A | 7/1981 | Mizumoto | |
| 4,431,005 A | 2/1984 | McCormick | |
| 4,689,621 A | 8/1987 | Kleinberg | |
| 4,844,076 A | 7/1989 | Lesho et al. | |
| 5,279,607 A | 1/1994 | Schentag et al. | |
| 5,515,853 A | 5/1996 | Smith et al. | |
| 5,604,531 A | 2/1997 | Iddan et al. | |
| 5,643,175 A | 7/1997 | Adair | |
| 5,681,260 A * | 10/1997 | Ueda et al. | 600/114 |
| 5,697,377 A | 12/1997 | Wittkampf | |
| 5,747,996 A | 5/1998 | Fuchs | |
| 5,819,736 A | 10/1998 | Avny et al. | |
| 6,157,853 A * | 12/2000 | Blume et al. | 600/426 |
| 6,175,757 B1 * | 1/2001 | Watkins et al. | 600/425 |
| 6,188,355 B1 | 2/2001 | Gilboa | |
| 6,233,476 B1 | 5/2001 | Strommer et al. | |

(Continued)

FOREIGN PATENT DOCUMENTS

DE 34 40 177 5/1986

(Continued)

OTHER PUBLICATIONS

Robots for the Future—Shin-ichi, et al, Nov. 29, 2001.

(Continued)

*Primary Examiner* — Brian Casler
*Assistant Examiner* — Nasir Shahrestani
(74) *Attorney, Agent, or Firm* — Pearl Cohen Zedek Latzer, LLP

(57) ABSTRACT

A system and method for controlling a device in vivo. The system and method may utilize a steerable receiver, typically an element that is maneuverable by a magnetic field, for controlling the movement of a device, including the direction, force and velocity of the device movement.

14 Claims, 3 Drawing Sheets

U.S. PATENT DOCUMENTS

| | | | |
|---|---|---|---|
| 6,240,312 B1 | 5/2001 | Alfano et al. | |
| 6,304,769 B1 * | 10/2001 | Arenson et al. | 600/424 |
| 6,632,175 B1 * | 10/2003 | Marshall | 600/309 |
| 2001/0044578 A1 * | 11/2001 | Ben-Haim et al. | 600/424 |
| 2001/0051766 A1 | 12/2001 | Gazdzinski | |
| 2002/0120178 A1 * | 8/2002 | Tartaglia et al. | 600/114 |
| 2002/0165592 A1 | 11/2002 | Glukhovsky et al. | |
| 2003/0135112 A1 * | 7/2003 | Ritter et al. | 600/424 |

FOREIGN PATENT DOCUMENTS

| | | |
|---|---|---|
| DE | 43 13 843 | 11/1994 |
| JP | 55-103834 | 8/1980 |
| JP | 03-109022 | 5/1991 |
| JP | 04-022325 | 1/1992 |
| JP | 4109927 | 4/1992 |
| JP | 5015515 | 1/1993 |
| JP | 6114037 | 4/1994 |
| JP | 2001-179700 | 7/2001 |
| JP | 2001224553 | 8/2001 |
| JP | 2002000556 | 1/2002 |
| WO | WO 99/60370 | 11/1999 |
| WO | WO 00/10456 | 3/2000 |
| WO | WO 01/06917 | 2/2001 |
| WO | WO 01/08548 | 2/2001 |
| WO | WO 01/50941 | 7/2001 |

OTHER PUBLICATIONS

The Radio Pill, Rowlands, et al., British Communications and Electronics, Aug. 1960, pp. 598-601.
Video Camera to "TAKE"—RF System Lab, Dec. 25, 2001.
Wellesley company sends body montiors into space—Crum, Apr. 1998.
www.rfnorkia.com—NORIKA3, Dec. 24, 2001.
Wireless transmission of a color television moving image from the stomach using a miniature CCD camera, light source and microwave transmitter. Swain CP, Gong F, Mills TN. Gastrointest Endosc 1997;45:AB40.
BBC News Online—Pill camera to 'broadcast from the gut', Feb. 21, 2000, www.news.bbc.co.uk.
Weitschies, et al., Magnetic marker monitoring of disintegrating capsules, European Journal of Pharmaceutical Sciences 13, 411-416, 2001.
European Search Report for Application No. EP 02 77 2784 dated Oct. 20, 2008.
Japan Office Action for Application No. 2003-531620 dated Jan. 13, 2009.
Japanese Office Action, issued Oct. 12, 2010, for Japanese Patent Application No. 2003-531620.

* cited by examiner

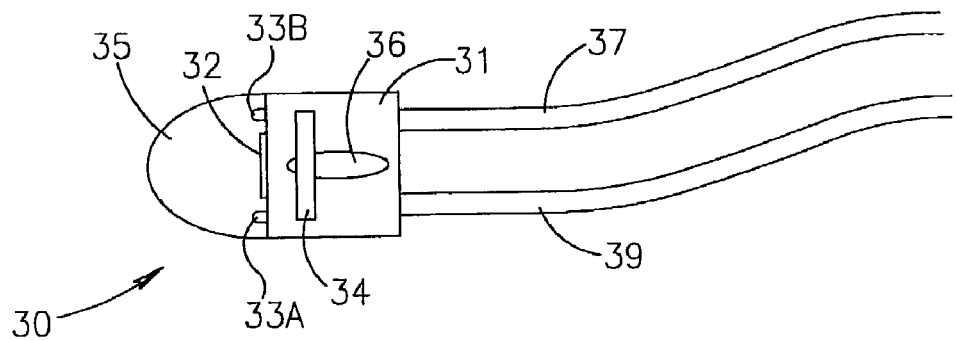
FIG.3
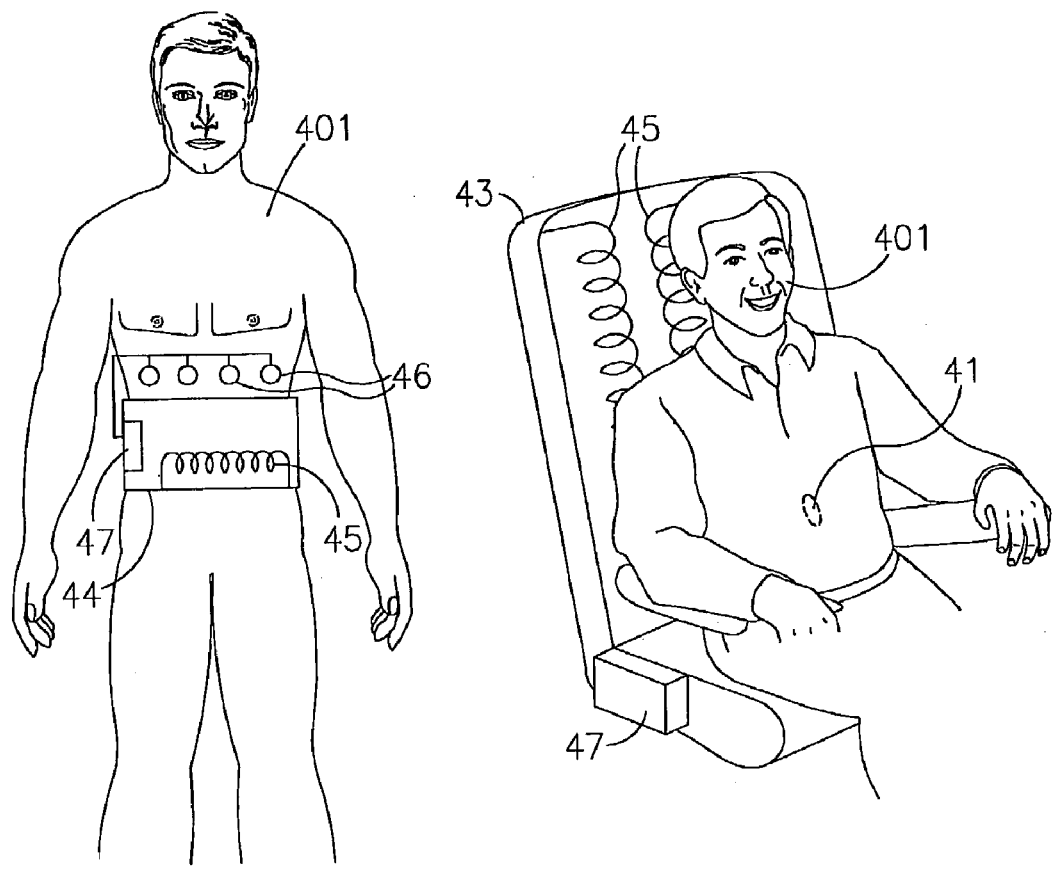
FIG.4B
FIG.4A

SYSTEM AND METHOD FOR CONTROLLING A DEVICE IN VIVO

PRIOR PROVISIONAL APPLICATION

The present application claims benefit from prior provisional application No. 60/324,067 entitled "SYSTEM AND METHOD FOR CONTROLLING A DEVICE IN VIVO" and filed on Sep. 24, 2001.

FIELD OF THE INVENTION

The present invention relates to the field of in vivo devices. More specifically, the present invention relates to a system and method for positioning and controlling a device in vivo.

BACKGROUND OF THE INVENTION

In vivo devices can be used in diagnostic and/or therapeutic processes with minimal intrusion. These devices may include in vivo tools or sensors, such as in vivo imaging devices, in vivo pH meters etc. Typically, in vivo devices, such as endoscopes, are advanced through a body lumen by being pushed or pulled by an external operator. Autonomous in vivo devices, such as gastrointestinal capsules, are typically moved through the gastrointestinal (GI) tract by the natural action of peristalsis. Autonomous devices typically include an internal power source, such as a battery. However, transfer of energy from an external source to in vivo devices is possible. For example, an external time-varied magnetic field may be created in the vicinity of a body in which a device has an electric generator disposed within the device. The magnetic field is typically used to rotate a rotor inside the device, the rotated rotor then being used to generate electric current. Another external pumped power source may be a remote microwave delivery system comprising EM antennae or receivers with high absorption coefficient and resonance geometrical arrangement built inside the device to collect external microwave energy at a designated wavelength. Still another external pumped power source is a remote ultrasound delivery system comprising piezoelectric receivers built inside the device to collect external ultrasonic energy to power the device and to charge-up an internal battery.

There is a need for an improved system and method for controlling and maneuvering in vivo devices.

SUMMARY OF THE INVENTION

Embodiments of the present invention provide a system and method for controlling a device in vivo. Optionally, embodiments of the system and method are used for locating and/or positioning a device in vivo. Typically, embodiments of the system and method of the invention utilize an element, such as a steerable receiver for controlling the movement of a device, including the direction, force and velocity of the device movement.

Generally, the term "location" refers to the place of the device in relation to a patient's anatomy whereas the term "position" refers to the three dimensional location of the device typically with six degrees of freedom, much the same as used to describe the maneuvers of, for example, a remotely piloted vehicle (RPV).

A system according to an embodiment of the invention includes an in vivo device and a signal source. The in vivo device includes a steerable receiver and the signal source, which is typically external to a patient's body, transmits at least a first signal having a first vector that is received by the steerable receiver. The steerable receiver responds to the signal by, for example, rotating or otherwise moving in accordance with the vector of the signal. Furthermore, other components of the signal, for example the amplitude of the signal, can effect the movement of the device. The rotary or other motion of the receiver will, in turn, cause the in vivo device to be steered in accordance with the signal.

According to a further embodiment of the invention the in vivo device includes, in addition to the steerable receiver, a transmitter which can transmit at least a first positional signal to an external receiving system. Alternately, the in vivo device may include a steerable transceiver for transmitting a positional signal and for receiving a signal having a vector. Thus, the location and/or position of the in vivo device can be determined, for example, by receiving at least one positional signal from the transmitter or transceiver and the in vivo device can be steered in accordance with the determined location and/or position of the in vivo device. The system may further include a processing unit that is in communication with the receiving system for calculating the location and/or position of the in vivo device. The processing unit may also be in communication with an in vivo sensor for processing data relating to the in vivo environment. Furthermore, the processing unit may be in communication with the signal source for inducing a signal.

A method according to an embodiment of the invention includes the steps of exposing an in vivo device, which includes a steerable receiver, to at least one signal having a vector and receiving the at least one signal via the steerable receiver. The method may further include the steps of transmitting at least one positional signal for determining the location and/or position of the in vivo device prior to the step of exposing an in vivo device to at least one signal having a vector. Further, the method may include the steps of processing the positional signal and communicating a command to a signal source to transmit a signal having a vector in accordance with the processed positional signal.

The signal having a vector is typically a component of an electric or electromagnetic field and the steerable receiver or transceiver is typically a coil or magnet having a dipole.

According to one embodiment of the invention the system includes an autonomous in vivo device, optionally an in vivo sensing device, such as an image sensor, a pH meter, a pressure detector, a thermometer etc., which includes at least one steerable receiver for receiving a signal having a vector and a signal source for generating at least one signal having a vector. The in vivo device may also include at least one transmitter for transmitting position information, typically three dimensional or six degrees of freedom position information, of the autonomous in vivo device at any given time and/or for transmitting data from the sensing device; a receiving unit for receiving position information and optionally for receiving data from the sensing device; and a processing unit for computing the position and/or orientation of the imaging device at any given time and/or for controlling the signal source. The signal having a vector and/or the position information and/or the data from the sensing device can be transmitted wirelessly or through a wired connection to a receiving unit. The autonomous in vivo device may be a swallowable capsule capable of sensing the GI environment and/or capable of performing in vivo procedures.

According to one embodiment of the invention the system includes a swallowable capsule for imaging the gastrointestinal (GI) tract. The capsule electrical elements, which are typically battery powered, include an illumination unit for illuminating in vivo sites, an image sensor for obtaining in vivo images, a steerable receiver for receiving a signal having a vector and a transmitter for wirelessly transmitting image data and position data to an external processing unit. Alternately, the capsule includes a steerable transceiver for transmitting position information and receiving a signal having a vector and a separate transmitter for transmitting image data. Such an in vivo image sensor can provide an external operator with a real time view of a body lumen. The signal having a vector can be controlled by the external operator (e.g., by using a joy stick) enabling the operator to maneuver the image sensor to any part of the lumen guided by the real time images of the lumen.

BRIEF DESCRIPTION OF THE DRAWINGS

The present invention will be understood and appreciated more fully from the following detailed description taken in conjunction with the drawings in which:

FIG. 3 is a schematic illustration of a device in accordance with another embodiment of the invention; and FIGS. 4A and B are schematic illustrations of a system according to additional embodiments of the invention; in FIG. 4A with a stationary signal source and in FIG. 4B with a mobile or portable signal source.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Embodiments of the present invention may enable movement of a diagnostic and/or therapeutic device, such as a swallowable video capsule, an endoscope, a needle, a stent etc. Movement may be facilitated, through, for example, difficult to access parts of the body.

Figure 1A:
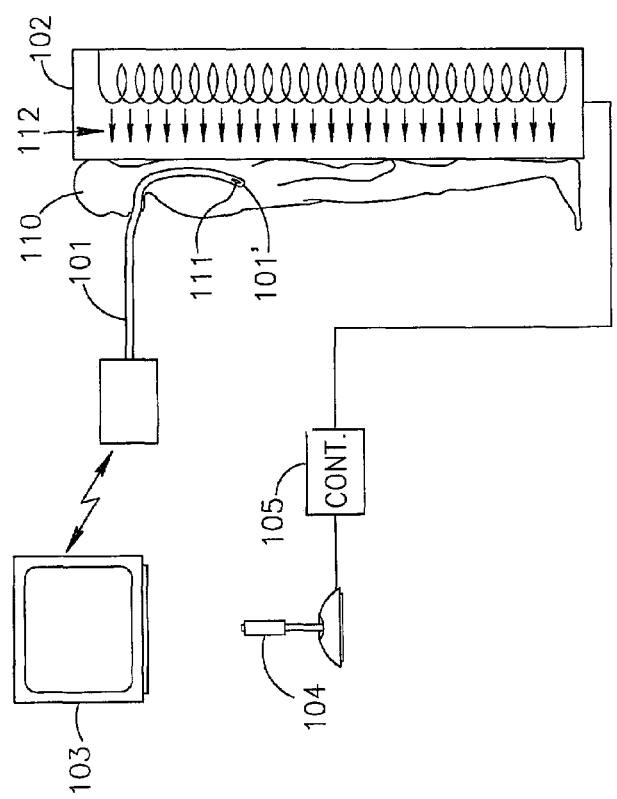
FIG. 1A is a schematic illustration of a system according to an embodiment of the invention.

A system according to one embodiment of the invention is schematically illustrated in FIG. 1A. The system includes, for example, an in vivo device 101 having a steerable receiver 111, a signal source 102, a controller 105 having a user control, such as a joystick or handle, 104, for controlling the signal source and, typically, a monitor or display 103. The in vivo device 101, in the embodiment illustrated in FIG. 1A, is typically an endoscope or catheter that is inserted into a patient 110 for imaging and possibly otherwise sensing body lumens, such as the GI tract, blood vessels, the reproductive tract or any other suitable body lumens. Typically, the device 101 is flexible, in particular near its distal end. The device 101 may include typical controls, such as pulleys. In alternate embodiments, the device may be other devices, with other structures.

The in vivo device 101 typically includes a steerable receiver 111 that is typically located at the leading end 101' of the in vivo device 101. The steerable receiver 111 receives a signal 112 from the signal source 102 and may be rotated or moved according to such signal 112, which may include, for example, the vector and possibly other parameters. Other user controls may be used, such as buttons, graphical user interfaces used with computers, etc.

Figure 1B:
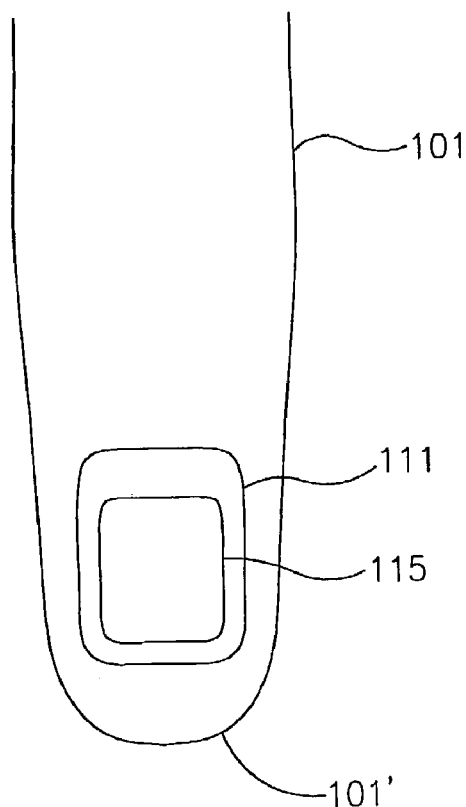
FIG. 1B is a schematic depiction of a steerable receiver according to an embodiment of the present invention.

The signal source 102 generates a signal 112. Typically the signal source 102 generates a variable magnetic field. FIG. 1B is a schematic depiction of a steerable receiver according to an embodiment of the present invention. The steerable receiver 111 typically includes a magnetic receiver 115 including one or more coils or magnets or magnetized material and typically having a dipole which, for example, may be influenced by, manipulated by, or moved by the magnetic field induced by the signal source 102, and may be aligned by this magnetic field. The materials used may be any suitable material influenced by a magnetic field. The signal source 102 can include an AC induction coil, e.g., a low frequency AC induction coil (about 60 Hz) or may have a rotating magnetic circuit to generate a varying magnetic field. In order to achieve higher efficiency of the energy transmission it may be desirable to operate in a relatively high frequency range. However, due to high attenuation of the body tissues at high frequencies—the practical frequency range may be from several tens of Hz to several tens of KHz.

The signal source 102, which may be, for example, a stationary or a mobile portable source, is placed in proximity to the patient's body, typically generating an electromagnetic field that substantially surrounds the patient's body. In other embodiments, the field need only surround the relevant portion of the patient, for example the abdomen. A magnetic field can be generated continuously or when necessary.

The in vivo device 101 typically includes an image sensor (not shown) such as a CCD or a CMOS image sensor, one or more illumination source(s) for illuminating an in vivo site (not shown) and optionally a transmitter (not shown) for, typically, wirelessly transmitting image data to a receiving/processing unit (not shown). The transmitter may operate by, for example, radio waves. Alternately, image data may be communicated through other systems, such as a wired connection to a receiving/processing unit (not shown). The receiving/processing unit may show an image or moving images on display 103, which may be, for example, a conventional monitor. Other methods and systems of image display may be used. The in vivo device 101 may include other sensors, such as a pH meter, temperature sensors, pressure sensors and so on, for sensing the endo-luminal environment. Sensed endo-luminal conditions may also be transmitted (wirelessly or not) to a receiving/processing unit and may be indicated on display 103. The same transmitter can be used for transmitting, for example, positional information and image (or other) data. Such positional information may typically include three dimensional or six degrees of freedom position information An operator can view the images and other information indicated on display 103 and can control the signal source 102 by manipulating control 104, to induce a signal having a desired vector and/or amplitude so as to steer the leading end 101' of the in vivo device to a desired location and/or position.

Examples of in vivo sensing systems that can be utilized in the present invention are described in U.S. Pat. No. 5,604,531 to Iddan and in International Application Publication No. WO 01/65995, both of which are assigned to the common assignee of the present invention and which are hereby incorporated by reference. The systems described above may be battery operated and wireless or may be connected to a power supply and/or light source external to the patient's 110 body. For example, a capsule as described in International Application Publication No. WO 01/65995 may be located at or near the leading end 101' to provide image or other information to the monitor 103.

Figure 2:
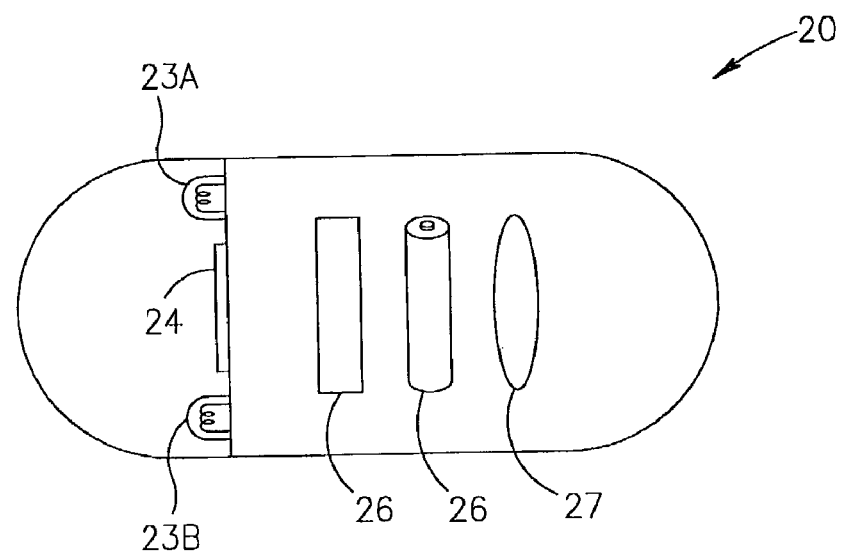
FIG. 2 is a schematic illustration of an in vivo device according to an embodiment of the invention.

An in vivo device in accordance with another embodiment of the invention is schematically illustrated in FIG. 2. The in vivo device 20 is, typically, a swallowable capsule, such as one similar to the embodiments described in the above mentioned U.S. Pat. No. 5,604,531 and International Application Publication No. WO 01/65995. The in-vivo device may be similar to systems other than described in U.S. Pat. No. 5,604,531 and International Application Publication No. WO 01/65995. The imaging device 20 includes, for example, an illumination unit, typically including one or more illumination source(s) such as white LEDs 23A and 23B, an image sensor 24, a transmitter 26 for transmitting image signals of the image sensor 24, a steerable transceiver 27, and a power source 25, such as a silver oxide battery, that provides power to the entirety of the electrical elements of the imaging device 20. Other components and configurations of components may be used.

The in vivo device 20 is typically capsule shaped, and typically can be easily swallowed and may passively pass through the entire GI tract. While passing through tube-like portions of the GI tract, such as the small intestine, the in vivo device 20 may be pushed along by natural peristalsis and may be restricted by the tube walls to a fixed orientation. As the in vivo device 20 passes through the small intestine it periodically images the tube wall. However, when the in vivo device 20 reaches cavities such as the stomach or the large intestine it may not be restricted by the lumen walls and it may, for example, rotate and tumble through the lumen. Also, in these lumens the natural movement may not always be effective in moving the capsule shaped device.

According to an embodiment of the invention, a signal source, such as a variable electromagnetic field generator that can be controlled by an external operator or automatically by a processing unit, transmits signals of varied vectors and amplitudes to the in vivo device 20 and moves the steerable transceiver 27 according to the signals sent. Methods of manipulating devices via signals, such as magnetic fields, are known in the art. The movement of the steerable transceiver 27 may, for example, cause the entire in vivo device 20 to be moved in a desired direction, pitch, yaw, roll etc. In one embodiment, the direction, force, velocity and orientation of the in vivo device 20 may be controlled. For example, increasing the variable magnetic vector of the signal may steer the in vivo device in the direction of the signal vector. The desired direction can be determined by an external operator or automatically, in accordance with position or other data of the in vivo device 20.

The processing unit may be part of a feedback cycle in which positional data and/or in vivo environment data can induce a specific signal. For example, the location or position of the device may be determined, for example by the processing unit (as further detailed below). If the location or position of the device is undesired (e.g., the device is facing and sensing one wall of a body lumen whereas it is desired to sense other walls of the body lumen) the processing unit can communicate a command, such as an electric or any other suitable (such as microwave, IR etc.) signal, to a processor in the signal source to transmit a signal having a vector and/or amplitude appropriate for steering the in vivo device in a desired direction or to a desired location and/or position. In another case, environmental conditions, such as in vivo pH or temperature, as determined by an in vivo sensor, may indicate that it is desirable for the in vivo device to be slowed down for further inspection of the specific site. The processing unit may be triggered by any of these environmental conditions to communicate a command, as described above, and a signal may be induced accordingly.

In accordance with an embodiment of the invention, an in vivo device can be programmed to follow a predefined route in vivo. A predetermined route may include pre-programmed parameters, such as, the time period the device should spend in different portions of the in vivo route. Alternately, the route of the device in vivo can be corrected in response to on line positional or other data received from the in vivo device. For example, an ingestible capsule, according to one embodiment of the invention, may be delayed in a specific portion of the GI tract, such as in the sack-like secum. Positional information sent from the capsule compared, for example, with a time analysis of the capsule stay in the body, may indicate to an operator that the capsule has not yet reached an expected portion of the GI tract and the capsule may be maneuvered by the operator to exit the secum to resume its passage through the GI tract. In accordance with another embodiment of the invention the in vivo device is an imaging device that periodically images a body lumen, and the route of the device in vivo can be controlled in accordance with the real time images that are received from the device. The in vivo imaging device can be controlled, according to embodiments of the invention and as described above, to be slowed down, retreated, turned etc. for obtaining additional images of a site, for example a site of a suspected pathology, that was imaged by the device. Also, an in vivo device can be slowed down or fully arrested, retreated, turned etc. for obtaining a sample or releasing a substance, such as a probe or a medicament, at a site determined to be suitable, by images or other environmental indications.

The location and/or position of the in vivo device 20 can be determined by, for example, utilizing the steerable transceiver 27. Known methods for determining the in vivo position of objects can be utilized in embodiments of the present invention. Examples of position monitoring systems that can be easily adjusted for use with embodiments of the present invention are described in U.S. Pat. No. 5,697,377 to Wittkampf, U.S. Pat. No. 5,515,853 to Smith and U.S. Pat. No. 6,188,355 to Gilboa. These US patents are hereby incorporated by reference. Other methods may be used. Examples of calculation methods for determining the three dimensional position or location of a device containing transceiver 27 that are applicable in embodiments of the present invention are described in WO 01/06917 to Gilboa and WO 00/10456 to Blecher et al. Both publications are hereby incorporated by reference. Other methods may be used. It will be appreciated that such position to calculations may be carried out on suitable computational or processing devices.

In one embodiment, the steerable transceiver 27 may include three electrodes, coils or transponders that receive electromagnetic signals transmitted from an external source. The external source may include three electromagnetic transmitters, each located at a fixed position in an external reference frame that transmit three distinguishable electromagnetic radiations (such as at different frequencies). The three electrodes, coils or transponders receive signals corresponding to the electromagnetic radiations at a plurality of times, each of the signals including components of at least one of the three radiations. The three electrodes, coils or transponders form functions that include the components of the signal received by the each electrode from the three transmitters. The position and the orientation of the in vivo device 20 can be inferred from the functions, as further elaborated in the above mentioned U.S. Pat. No. 6,188,355.

Other position monitoring systems and methods may be used with embodiments of the present invention, such as through using monitors that include ultrasound transceivers or monitors that include three magnetic coils that receive and transmit positional signals relative to an external constant magnetic field. For example, magnetic marker monitoring techniques may be used as described in a paper published by Weitschies et al. (Weitschies et al (2001) *European Journal of Pharmaceutical Sciences* 13, 411-416), which is hereby incorporated by reference.

An in vivo device according to another embodiment of the invention is schematically described in FIG. 3. Imaging device 30 includes, for example, a body 31 having an optical window 35. The imaging device 30 includes an image sensor 32 (e.g., a CMOS or CCD) and an optical system, which typically includes lenses (not shown) and one or more illumination source(s) 33A and 33B, all of which are positioned behind the optical window 35. Further, the imaging device 30 includes a steerable receiver 36, for example, as described above, and a transmitter 34 for transmitting image or other data to a receiving system, which is external to a patient's body. The transmitter may operate by, for example, radio waves. Imaging device 30 is typically powered through a wire 37 that extends from the rear end of body 31 and that is connected to a power source, typically external to a patient's body (not shown). Also, imaging device 30, specifically the illumination source(s) 33A and 33B, may be connected to a light source external to a patient's body (not shown), through, for example, optical fibers 39. Alternately, light sources internal to the imaging device, such as LEDs, may be used. Additional wires or tubes can be extended from body 31, for example, working channels or a wire connected to an external receiving system for receiving data from the transmitter 34.

Imaging device 30 can be inserted in a body lumen for in vivo imaging of the lumen. For example, imaging device 30 can be inserted into a patient's GI tract for imaging the GI tract. The imaging device's 30 route in the GI tract is may be limited due to, for example, the wires 37 and 39 extending from it. However, the imaging device 30, which can be of a smaller diameter and more easily maneuvered than devices presently used for examining the GI tract, may enable close scrutiny of the GI tract which is an improvement over known methods of examining the large intestine, such as endoscopy or colonoscopy. For example, a device as described above can be maneuvered through the large intestine by being inserted into a patient much like a suppository is inserted and by being "pulled" through the large intestine according to an embodiment of the method of the invention. In the same manner, an endoscope can be maneuvered through a patient's intestine, eliminating the need to push the endoscope in a manner that is painful to the patient. Alternately, a system according to embodiments of the invention may aid the pushing.

A system according to another embodiment of the invention is schematically illustrated in FIGS. 4A and 4B. As shown in FIG. 4A, a patient 401 swallows a capsule 41 as described above. While the capsule 41 is sensing the patient's 401 GI tract the patient 401 is, for example, seated or laid on a seat or bed 43, or wears a garment which includes a magnetic field generator 45, a processing and control unit 47 and possibly a position monitoring system, such as or similar to the systems described above. A magnetic field can be generated continuously or when necessary.

The processing and control unit 47 is, for example, input with positional data from the monitoring system or is controlled by an external operator to maneuver the capsule 41 to a desired location or three dimensional position. In one embodiment, the processing and control unit 47 may generate a first signal that is sent to the device, for maneuvering the device at a known direction or velocity. The first signal is a known signal with an expected end result on the capsule 41 position. The processing and control unit 47 can correct the position of the capsule 41 by, for example, comparing the first generated signal (which is expected to bring the device to a certain position) and the actual position of the capsule 41 at any given moment (as determined, for example, by the position monitoring system). For example, when the capsule 41 movement in the GI tract is stopped (due to, for example, being blocked by the GI tract wall or due to not being moved by the natural movement of the intestine), the processing and control unit 47 can determine that the capsule is not moving. This may be determined for example, by the above described comparison between the expected and actual position after sending a first signal, or by utilizing a motion detector in the device, or by comparing positional information or image information at different time points or by other methods known in the art. An automatic command from the processing and control unit 47 can be sent to the magnetic field generator 45 to transmit a signal of an amplitude and vector that will be enough to move or rotate the capsule 41 but not, for example, to harm the GI tract wall. Alternately, an operator can be alerted by the processing and control unit 47 that the capsule 41 is not moving and the operator can manually (for example with a joy stick) command an appropriate signal to be generated. The operator can be aided by real time images that are transmitted from the capsule 41.

In an alternate embodiment, schematically shown in FIG. 4B, a magnetic field generator 45, a processing and control unit 47 and a position monitoring system can be incorporated into a garment, such as a belt or jacket 44 worn around the appropriate area of the patient's 401 body. Thus, the system is portable and a patient 401 is free to move about while the capsule 41 is sensing the GI tract. In this embodiment a number of reference points are typically attached to the patient 401 (such as antennas 46 attached to a plurality of points on the patient's body) for the processing and control unit 47 to be able to take into account artifacts generated by the patient's movements.

It will be appreciated by persons skilled in the art that the present invention is not limited by what has been particularly shown and described herein above. Rather the scope of the invention is defined by the claims which follow.

The invention claimed is:
1. A system for magnetically maneuvering an imaging device in the GI tract, the system comprising:
   an imaging device, said device comprising a steering element, said steering element configured to be maneuvered by a magnetic field, an image sensor, an illumination source and a transmitter configured to transmit image signals of the image sensor;
   a receiving system configured to receive the transmitted image signals;
   a signal source, located externally to a patient's body, configured to generate at least one signal that maneuvers the steering element; and
   a processor in communication with the imaging device and with the signal source, configured to automatically determine a desired position for the imaging device, configured to compare the position of the imaging device with the desired position for the imaging device, and, based on the comparison, configured to automatically cause the signal source to generate the at least one signal to remotely and magnetically maneuver the steering element in the GI tract.
2. The system according to claim 1 wherein the processor is configured to control the route of the imaging device in accordance with image signals received from the imaging device.

3. The system according to claim 1 wherein the imaging device is a swallowable capsule.

4. The system according to claim 1 wherein the signal source is a variable magnetic field generator.

5. A method for magnetically maneuvering a swallowable imaging capsule in the GI tract, the method comprising:
   receiving data relating to the position of the imaging capsule; and
   in a processor, automatically determining a desired position for the imaging capsule, comparing the position of the imaging capsule with the desired position for the imaging capsule, and, based on the comparison, automatically causing a signal source to produce a magnetic signal to remotely and magnetically maneuver said swallowable imaging capsule in the GI tract.

6. The method according to claim 5 wherein the route of the imaging capsule is controlled in accordance with image signals received from the imaging device.

7. The system of claim 1, wherein the steering element comprises a coil.

8. The system of claim 1, wherein the steering element comprises a magnet having a dipole.

9. The system of claim 1, wherein the transmitter is configured to transmit a positional signal.

10. The system of claim 1, wherein the processor is configured to calculate the position of the imaging device.

11. The method of claim 5, wherein the swallowable imaging capsule is magnetically maneuvered using a coil.

12. The method of claim 5, wherein the swallowable imaging capsule is magnetically maneuvered using a magnet having a dipole.

13. The method of claim 5, wherein the data relating to the position of the imaging capsule is received from a transmitter configured to transmit a positional signal.

14. The method of claim 5, comprising calculating the position of the imaging capsule.

\* \* \* \* \*